(12) United States Patent
Park et al.

(10) Patent No.: US 10,677,784 B2
(45) Date of Patent: Jun. 9, 2020

(54) APPARATUS FOR MANUFACTURING DISPLAY MODULE

(71) Applicant: LG CHEM, LTD., Seoul (KR)

(72) Inventors: San Park, Daejeon (KR); Jea Han Ryoo, Daejeon (KR); Bong Su Jeung, Daejeon (KR); Cheon Ho Park, Daejeon (KR); Beom Seok Lee, Daejeon (KR)

(73) Assignee: LG CHEM, LTD., Seoul (KR)

( * ) Notice: Subject to any disclaimer, the term of this patent is extended or adjusted under 35 U.S.C. 154(b) by 6 days.

(21) Appl. No.: 15/554,330

(22) PCT Filed: Nov. 18, 2016

(86) PCT No.: PCT/KR2016/013305
§ 371 (c)(1),
(2) Date: Aug. 29, 2017

(87) PCT Pub. No.: WO2017/086726
PCT Pub. Date: May 26, 2017

(65) Prior Publication Data
US 2018/0044557 A1 Feb. 15, 2018

(30) Foreign Application Priority Data
Nov. 19, 2015 (KR) .................. 10-2015-0162724

(51) Int. Cl.
*B32B 43/00* (2006.01)
*G01N 33/50* (2006.01)
(Continued)

(52) U.S. Cl.
CPC ............ *G01N 33/5058* (2013.01); *A47L 9/00* (2013.01); *C09J 7/40* (2018.01); *G01N 1/30* (2013.01);
(Continued)

(58) Field of Classification Search
CPC . B32B 38/10; B32B 43/006; Y10T 156/1132; Y10T 156/1174;
(Continued)

(56) References Cited

U.S. PATENT DOCUMENTS

| 6,172,528 B1 | 1/2001 | Malarsie |
| 6,478,919 B1 | 11/2002 | Kawada et al. |
| 2013/0269869 A1 | 10/2013 | Hirata et al. |

FOREIGN PATENT DOCUMENTS

| CN | 103492936 A | 1/2014 |
| JP | 2000-353472 A | 12/2000 |

(Continued)

*Primary Examiner* — Mark A Osele
*Assistant Examiner* — Nickolas R Harm
(74) *Attorney, Agent, or Firm* — Dentons US LLP

(57) ABSTRACT

Disclosed is an apparatus for manufacturing a display module. An apparatus for manufacturing a display module according to an exemplary embodiment of the present invention, which attaches a polarizing plate, from which a release film is peeled, onto a display panel, includes: a separator configured to peel a release film from a polarizing plate, and formed with a flow path, through which foreign substances dropped from the release film when the release film is peeled are dischargeable; and a suction unit coupled to the separator to suck the foreign substances.

4 Claims, 3 Drawing Sheets

(51) Int. Cl.
*C09J 7/40* (2018.01)
*A47L 9/00* (2006.01)
*G02B 5/30* (2006.01)
*G02F 1/1335* (2006.01)
*G01N 1/30* (2006.01)
*B32B 38/10* (2006.01)

(52) U.S. Cl.
CPC ............. *G02B 5/30* (2013.01); *G02F 1/1335* (2013.01); *B32B 38/10* (2013.01); *B32B 43/006* (2013.01); *G01N 2333/33* (2013.01); *Y10T 156/1132* (2015.01); *Y10T 156/1174* (2015.01); *Y10T 156/1195* (2015.01); *Y10T 156/195* (2015.01); *Y10T 156/1944* (2015.01); *Y10T 156/1994* (2015.01)

(58) Field of Classification Search
CPC ......... Y10T 156/1195; Y10T 156/1944; Y10T 156/195; Y10T 156/1994

USPC ................ 156/707, 715, 719, 758, 759, 767
See application file for complete search history.

(56) References Cited

FOREIGN PATENT DOCUMENTS

| | | |
|---|---|---|
| JP | 2012234014 A | 11/2012 |
| JP | 2015-025948 A | 2/2015 |
| KR | 10-2001-0039647 A | 5/2001 |
| KR | 100393473 B1 | 8/2003 |
| KR | 1020070090422 A | 9/2007 |
| KR | 1020080010552 A | 1/2008 |
| KR | 10-2010-0067910 A | 6/2010 |
| KR | 10-2013-0116808 A | 10/2013 |
| KR | 10-2013-0119404 A | 10/2013 |
| KR | 10-2014-0035635 A | 3/2014 |
| TW | 452825 B | 9/2001 |

[Figure 1]
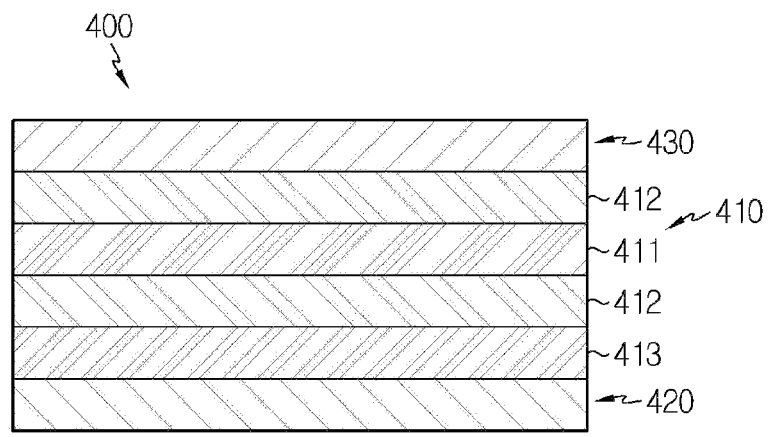
[Figure 2]
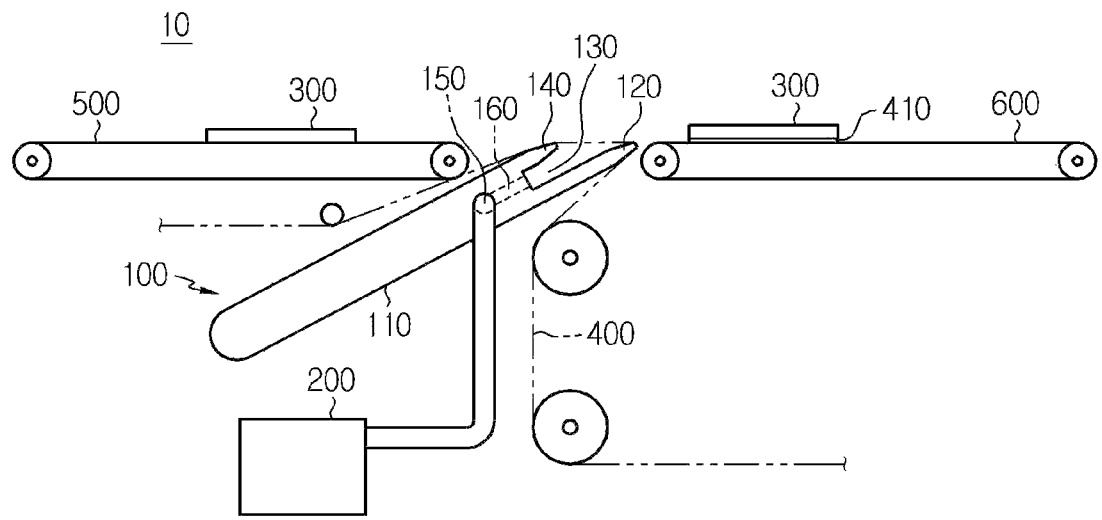

[Figure 3]
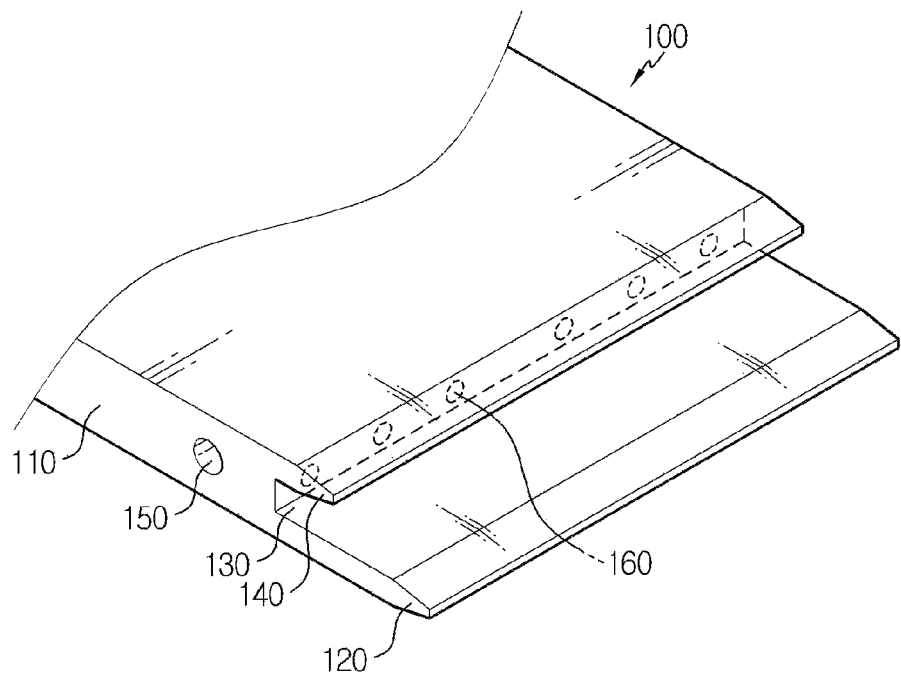
[Figure 4]
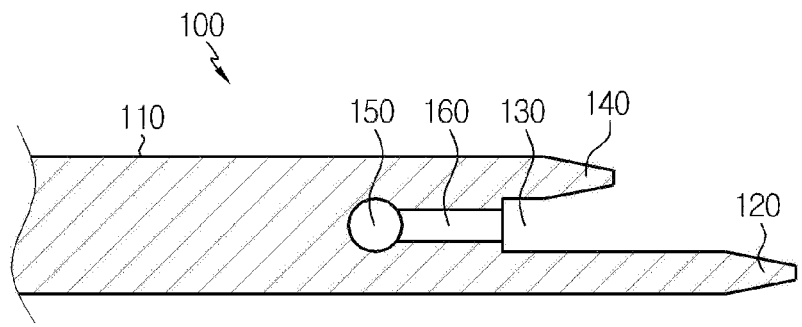

[Figure 5]
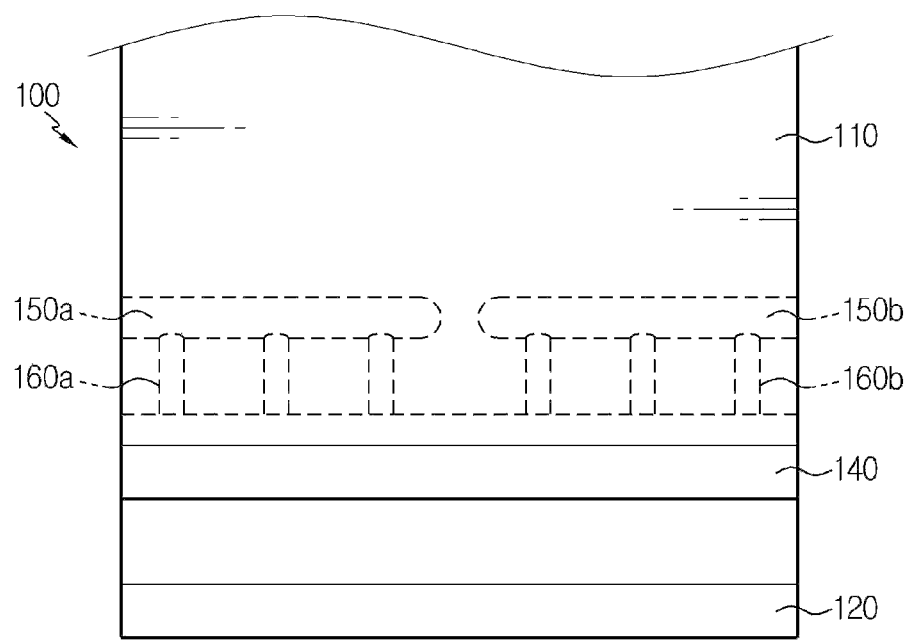
[Figure 6]
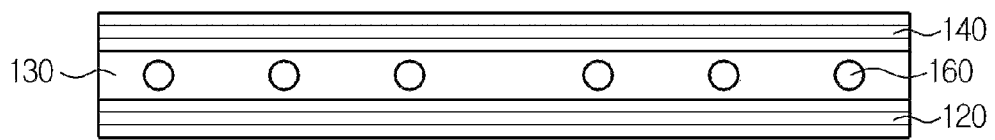

APPARATUS FOR MANUFACTURING DISPLAY MODULE

This application is a National Stage Application of International Application No. PCT/KR2016/013305 filed on Nov. 18, 2016, which claims the benefit of Korean Patent Application No. 10-2015-0162724, filed on Nov. 19, 2015, which is hereby incorporated by reference in its entirety for all purposes as if fully set forth herein.

TECHNICAL FIELD

The present invention relates to an apparatus for manufacturing a display module, and more particularly, to an apparatus for manufacturing a display module, in which a suction unit is coupled to a separator formed with a flow path, through which foreign substances are dischargeable, so that the foreign substances may be easily discharged when a release film is peeled from a polarizing plate.

BACKGROUND ART

Recently, as an electronic display industry among the semiconductor industries has been rapidly developed, a flat panel display (FPD) appears.

The FPD is an image display device, which is thinner and lighter than that of a cathode ray tube (CRT) mainly used as a display of a TV or a computer monitor in a previous time, and includes a liquid crystal display (LCD), a plasma display panel (PDP), an organic light emitting diode (OLED), and the like.

Particularly, the LCD among the various kinds of FPDs for displaying information advantageously has a clear image and very low driving power, and is easily applied to a small information device, so that a necessity thereof is considerably increased.

Further, according to the regulation of the transmission of broadcasting for a high definition television (HDTV), in order to satisfy a purchase need of a user desiring to view a clear image, research and development of the LCD has been continuously conducted.

In general, the LCD includes a display panel, which is capable of displaying an electric signal in a form of an image. A polarizing plate for assigning an optical characteristic is attached onto an external surface of the display panel, and polarizes light, which vibrates in all of the directions, to light, which vibrates only in a specific direction, and implements a desired image. That is, the polarizing plate is an optical film used in an LCD of a PC, a notebook computer, a mobile phone, and a camcorder, and the polarizing plates are positioned at both sides of the LCD and determine an optical characteristic of the LCD through a function of allowing only light of a desired direction component to pass through according to a voltage on/off of the LCD.

A release film for protecting an adhesive layer may be attached onto the polarizing plate, and after the release film is peeled and removed from the polarizing plate, the polarizing plate is attached to the display panel. Here, when the release film is peeled from the polarizing plate, foreign substances, such as adhesive ingredients existing in the polarizing plate, may be dropped or scattered, and flow into an attachment region of the display panel and the polarizing plate, thereby increasing a defective rate of the attachment of the polarizing plate and decreasing a yield.

In the related art, in order to solve the problem, dropped or scattered foreign substances are sucked by installing a separate suction device provided with a nozzle. However, an attachment portion of the display panel and the polarizing plate is small, so that a space, in which the nozzle may be positioned, is limited, so that suction efficiency is degraded, and further, it is necessary to endure inconvenience that an installation position of the nozzle of the suction device is continuously changed according to a change in a width of the polarizing plate according to a change in a model of the panel.

DETAILED DESCRIPTION OF THE INVENTION

Technical Problem

Accordingly, a technical object to be achieved by the present invention is to provide an apparatus for manufacturing a display module, in which a suction unit is coupled to a separator formed with a flow path, through which foreign substances are dischargeable, so that the foreign substances may be easily discharged when a release film is peeled from a polarizing plate.

Further, a technical object to be achieved by the present invention is to provide an apparatus for manufacturing a display module, in which foreign substances are dischargeable through a flow path formed in a separator, thereby guaranteeing predetermined suction efficiency, regardless of the degree of smallness of a space.

Further, a technical object to be achieved by the present invention is to provide an apparatus for manufacturing a display module, it is not necessary to change a position of a suction unit, regardless of a change in a model of a panel, thereby simply and easily suctioning foreign substances.

Technical Solution

In accordance with one aspect of the present invention, there is provided an apparatus for manufacturing a display module, which attaches a polarizing plate, from which a release film is peeled, onto a display panel, the apparatus including: a separator configured to peel a release film from a polarizing plate, wherein the separator has a flow path, through which foreign substances dropped from the release film when the release film is peeled are dischargeable; and a suction unit coupled to the separator to suck the foreign substances.

The separator may include: a main body; a peeling part, which is extended from the main body in a longitudinal direction, and is in contact with the release film to peel the release film from the polarizing plate; and a first flow path formed between the peeling part and the main body so that the foreign substances are dischargeable.

The separator may further include a scattering preventing part, wherein the scattering preventing part is spaced apart from the peeling part, and is extended from the main body in the longitudinal direction so as to correspond to the peeling part, and prevents the foreign substances from being scattered to the outside.

The separator may further include: a second flow path passing through at least a part of an internal side of the main body; and a through-hole passing from the first flow path to the second flow path so that the foreign substances of the first flow path are movable to the second flow path.

The second flow path may be provided in a pair, and the pair of second flow paths may be separated from each other based on a center portion of the main body and may be positioned so as to face each other.

The suction unit may be coupled to the second flow path.

The suction unit may include a vacuum ejector or a vacuum pump.

In accordance with another aspect of the present invention, there are provided a display module manufactured by the apparatus for manufacturing the display module, and a display device including the display module.

Advantageous Effects

According to the exemplary embodiments of the present invention, the suction unit is coupled to the separator formed with the flow path, through which foreign substances are dischargeable, and the suction unit is operated when the release film is peeled from the polarizing plate, so that the foreign substances may be easily discharged through the flow path.

Further, foreign substances may be discharged through the flow path formed in the separator without a need of a separate suction device provided with a nozzle, so that it is possible to guarantee predetermined suction efficiency regardless of the degree of smallness of a space.

Further, the suction unit is coupled to the separator, so that it is not necessary to change a position of the suction unit regardless of a change in a model of a panel, and it is possible to simplify and ease the suction of foreign substances.

BRIEF DESCRIPTION OF DRAWINGS

FIG. 1 is a cross-sectional view illustrating a schematic structure of a general polarizing plate assembly.

FIG. 2 is a schematic side view of a display module manufacturing apparatus according to an exemplary embodiment of the present invention.

FIG. 3 is a schematic perspective view of a separator in the display module manufacturing apparatus according to the exemplary embodiment of the present invention.

FIG. 4 is a schematic lateral cross-sectional view of a separator in the display module manufacturing apparatus according to the exemplary embodiment of the present invention.

FIG. 5 is a schematic top plan view of the separator in the display module manufacturing apparatus according to the exemplary embodiment of the present invention.

FIG. 6 is a schematic front view of the separator in the display module manufacturing apparatus according to the exemplary embodiment of the present invention.

MODE FOR INVENTION

Hereinafter, a display module manufacturing apparatus according to the exemplary embodiment of the present invention will be described in detail with reference to the accompanying drawings.

Terms or words used in the present specification and claims should not be interpreted as being limited to typical or dictionary meanings, but should be interpreted as having meanings and concepts which comply with the technical spirit of the present invention, based on the principle that an inventor can appropriately define the concept of the term to describe his/her own invention in the best manner. Therefore, configurations illustrated in the embodiments and the drawings described in the present specification are only the most preferred embodiment of the present invention and do not represent all of the technical spirit of the present invention, and thus it is to be understood that various equivalent and modified examples, which may replace the configurations, are possible when filing the present application.

In the drawing, a size of each element constituent or a specific part of the element is exaggerated, omitted, or schematically illustrated for convenience and clarity of description. Therefore, an actual size is not fully reflected to the size of each component. When it is determined that detailed explanation of known related functions or constitutions obscures the subject matter of the present invention, the explanation may be omitted.

The term, "coupled" or "connected" used in the present specification includes a case where one member is directly coupled or directly connected to another member, and a case where one member is indirectly coupled or indirectly connected to another member through a linking member.

FIG. 1 is a cross-sectional view illustrating a schematic structure of a general polarizing plate assembly.

Referring to FIG. 1, a polarizing plate assembly body 400 includes a polarizing plate 410 and a release film 420, and may further include a protective film 430 attached onto the polarizing plate 410 so as to protect the polarizing plate 410.

The polarizing plate 410 may include a polarizing film 411, a protective supporting film 412, and an adhesive layer 413. The polarizing film 411 is provided to polarize incident light in a predetermined direction, and may be formed of poly vinyl alcohol (PVA), in which an iodine material is aligned. Further, the protective supporting film 412 is attached to both surfaces of the polarizing film 411 to protect and support the polarizing film 411, and may be formed of a tri acetyl cellulose film that is an isotropic film corresponding to an optical film. Further, the adhesive layer 413 may be coupled to the protective supporting film 412, and may contain an adhesive ingredient and be coupled to a display panel 300.

Here, the release film 420, which is attached onto the adhesive layer 413 and protects the adhesive ingredient, may be coupled to the polarizing plate 410, and the release film 420 may be provided to be detached from and attached to the polarizing plate 410 by the adhesive layer 413.

FIG. 2 is a schematic side view of a display module manufacturing apparatus according to an exemplary embodiment of the present invention.

Referring to FIG. 2, in a display module manufacturing apparatus 10 according to an exemplary embodiment of the present invention, the polarizing plate 410, from which the release film 420 is peeled, is attached to the display panel 300, and first, the display panel 300 is moved to a side of a separator 100 by a supply conveyor 500. Further, the polarizing plate 410, onto which the release film 420 is attached, that is, the polarizing plate assembly 400, is provided to the separator 100, and the release film 420 is peeled from the polarizing plate 410 in the separator 100, and the polarizing plate 410 is coupled to a lower side of the display panel 300 through the adhesive layer 413. However, the polarizing plate 410 needs not to be essentially coupled to a lower side of the display panel 300, and as necessary, the polarizing plate 410 may be attached onto various portions of the display panel 300. Then, the display panel 300, onto which the polarizing plate 410 is attached, is loaded to the outside through a loading-out conveyor 600.

FIG. 3 is a schematic perspective view of a separator in the display module manufacturing apparatus according to the exemplary embodiment of the present invention, FIG. 4 is a schematic lateral cross-sectional view of a separator in the display module manufacturing apparatus according to the exemplary embodiment of the present invention, FIG. 5 is a schematic top plan view of the separator in the display module manufacturing apparatus according to the exemplary embodiment of the present invention, and FIG. 6 is a schematic front view of the separator in the display module manufacturing apparatus according to the exemplary embodiment of the present invention.

Referring to FIG. 2, the separator 100 peels the release film 420 from the polarizing plate 410. That is, when an attachment portion of the polarizing plate 410 and the release film 420 is in contact with the separator 100 and is pressurized, the release film 420 is peeled from the polarizing plate. In this case, the polarizing plate 410 and the release film 420 are bonded to each other by the adhesive layer 413, so that when the release film 420 is peeled from the polarizing plate 410, foreign substances, such as adhesive ingredients, existing in the polarizing plate 410 are scattered, and the scattered foreign substances flow into an attachment region of the display panel 300 and the polarizing plate 410 and contaminate a corresponding portion. Accordingly, the attachment portion of the display panel 300 and the polarizing plate 410 has a defect. In order to prevent the defect, referring to FIGS. 2 to 6, a flow path, through which foreign substances dropped from the release film 420 when the release film 420 is peeled from the polarizing plate 410 are dischargeable, is formed in the separator 100. That is, the foreign substances when the release film 420 is peeled from the polarizing plate 410 may be discharged to the outside through the flow path of the separator 100, so that it is possible to prevent the attachment portion of the display panel 300 and the polarizing plate 410 by the foreign substances from being contaminated.

The separator 100 may include a main body 110, a peeling part 120, and a first flow path 130. The main body 110 is formed with the elongated peeling part 120, and supports the peeling part 120. Further, the main body 110 may be fixed to other members by various methods, such as welding, bolting, and pin-engagement, and may have various shapes, which are capable of supporting the peeling part 120, and may be manufactured of various materials. The peeling part 120 is elongated from the main body 110 in a longitudinal direction, and is in contact with the release film 420 to peel the release film 420 from the polarizing plate 410. Further, the first flow path 130 is formed between the peeling part 120 and the main body 110. When a scattering preventing part 140, which is to be described below, is elongated from the main body 110, the first flow path 130 may be formed between the peeling part 120 and the scattering preventing part 140, but when the scattering preventing part 140 is not formed in the main body 110, the first flow path 130 may be formed between the peeling part 120 and the main body 110 in an opened form. In this case, a second flow path 150 may not be formed, and a suction unit 200 may be coupled to the first flow path 130. That is, the foreign substances are discharged to the outside through the first flow path 130 by the suction unit 200.

The scattering preventing part 140 may be elongated in the separator 100. When the scattering preventing part 140 is not formed, the foreign substances, such as adhesive ingredients, dropped from the polarizing plate 410 may be sucked into the suction unit 200 through the first flow path 130, but may also be scattered to the outside of the separator 100. In order to prevent the scattering of the foreign substances to the outside, the scattering preventing part 140 is spaced from the peeling part 120 and is elongated from the main body 110 in the longitudinal direction so as to correspond to the peeling part 120. For example, referring to FIG. 3, the peeling part 120 may be elongated from an end portion of the lower side of the main body 110 in the longitudinal direction, and the scattering preventing part 140 may be spaced apart from the peeling part 120 and is elongated from an end portion of an upper side of the main body 110 in the longitudinal direction, and the first flow path 130 may be formed between the peeling part 120 and the scattering preventing part 140.

The separator 100 may include a second flow path 150 and a through-hole 160. The second flow path 150 may pass through at least a part of an internal side of the main body 110. As illustrated in FIGS. 2 to 4, the second flow path 150 may be spaced apart from the first flow path 130 and may be formed to have a circular cross-section. However, this is simply one example, and the second flow path 150 may have various shapes. Further, the suction unit 200 may be coupled to the second flow path 150. Referring to FIG. 5, a pair of second flow paths 150 may be provided, and the pair of second flow paths 150a and 150b may be separated from each other based on a center portion of the main body 110. Further, as illustrated in FIG. 5, the pair of second flow paths 150a and 150b may be positioned while facing each other. However, the pair of second flow paths 150a and 150b does not need to be essentially separated, and one second flow path 150, which is connected from one end to the other end of the main body 110 and passes through the main body, may also be formed. Further, even though the second flow path is separated into the pair of second flow paths 150a and 150b, the pair of second flow paths 150a and 150b needs not to be positioned to face each other based on the center portion of the main body 110, and the pair of second flow paths 150a and 150b may also be asymmetrically positioned. In the meantime, the through hole 160 is formed in the main body 110 so as to pass from the first flow path 130 to the second flow path 150. That is, when the suction unit 200 coupled to the second flow path 150 is operated, the foreign substances flow into the first flow path 130 and then move to the second flow path 150 through the through-hole 160, and are discharged to the outside of the separator 100 through the second flow path 150. The through-hole 160 may be formed to be positioned at an inner side of a minimum width of the release film 420, based on a width of the release film 420, which has a minimum width among the models of the produced release films 420. As described above, the through-hole 160 is positioned at the inner side of the minimum width of the release film 420 because even though a size of the width of the release film 420 is increased, the through-hole 160 is still positioned at the inner side of the width of the release film 420, so that even though there is no separate action according to a change in a model, the foreign substances may easily move to the through-hole 160. However, when the through-hole 160 is positioned at an outer side of the width of the release film 420, the quantity of flow is concentrated to the through-hole 160 positioned at the outer side of the width of the release film 420, so that efficiency of the collection of foreign substances may be degraded. Accordingly, the through-hole 160 may be positioned at the inner side of the minimum width of the release film 420. However, as necessary, the position of the through-hole 160 may be variously changed. Here, referring to FIG. 5, when the second flow paths 150 are provided as the pair, through-holes 160a and 160b are also provided so as to correspond to the pair of second flow paths 150a and 150b and pass through the pair of second flow paths 150a and 150b, respectively. Referring to FIG. 2, the suction unit 200 is coupled to the separator 100 and sucks the foreign substances. The suction unit 200 may be variously provided, and for example, may be provided so as to include a vacuum ejector or a vacuum pump. When only the first flow path 130 is formed, the suction unit 200 may be coupled to the first flow path 130, but when all of the first flow path 130 and the second flow path 150 are formed, the suction unit 200 may be coupled to the second flow path 150. That is, when the suction unit 200 coupled to the second flow path 150 is operated, air is discharged to the outside from the first flow path 130 through the second flow path 150 along the through-hole 160. Here, the foreign substances dropped when the release film 420 is peeled from the polarizing plate 410 may be completely discharged to the outside of the separator 100 while moving from the first flow path 130 through the second flow path 150 along the through-hole 160 together with air.

In the related art, the attachment portion of the display panel 300 and the polarizing plate 410 is small, so that a space, in which the nozzle may be positioned, is small, and it is not easy to locate the nozzle in an accurate direction, so that suction efficiency is degraded. However, in the display module manufacturing apparatus 10 according to the exemplary embodiment of the present invention, the suction unit 200 is installed at the outside and is coupled to the second flow path 150 through a pipe and the like, so that it is possible to guarantee predetermined suction efficiency regardless of the degree of smallness of the space.

Further, in a separate suction device provided with a nozzle in the related art, the nozzle is adjacently installed to the display panel 300 and the polarizing plate 410, so that when a width of the polarizing plate 410 is changed according to a change in a model of the display panel 300, an installation position of the nozzle is continuously changed. However, in the display module manufacturing apparatus 10 according to the exemplary embodiment of the present invention, the suction unit 200 is coupled to the second flow path 150, so that even though a width of the polarizing plate 410 is changed according to a change in a model of the display panel 300, the installation position of the suction unit 200 is not influenced, thereby simplifying and easing the suction of foreign substances.

Hereinafter, the display module manufacturing apparatus 10 according to the exemplary embodiment of the present invention will be described.

Referring to FIG. 2, the display panel 300 having no attached polarizing plate 410 moves to the side of the separator 100 through the supply conveyor 500. Further, the release film 420 is peeled from the polarizing plate 410 in the separator 100, and the polarizing plate 410, from which the release film 420 is peeled, is attached onto, for example, a lower side of the display panel 300. Further, the display panel 300, onto which the polarizing plate 410 is attached, is loaded to the outside through the loading-out conveyor 600.

Here, the separator 100 is formed with the first flow path 130 between the peeling part 120 and the scattering preventing part 140, and the second flow path 150 passes through the internal side of the main body 110, and the first flow path 130 and the second flow path 150 are connected with each other through the through-hole 160. Further, the suction unit 200 is coupled to the second flow path 150.

That is, when the release film 420 is peeled from the polarizing plate 410, foreign substances, such as adhesive ingredients, existing in the polarizing plate 410 may be dropped, and the foreign substances are sucked to the suction unit 200 from the first flow path 130 along the second flow path 150 through the through-hole 160 and discharged to the outside of the separator 100, thereby preventing a defect by the foreign substances when the polarizing plate 410 is attached to the display panel 300.

In the meantime, a display module may be manufactured by attaching the polarizing plate 410 to the display panel 300, which is capable of displaying an electric signal in a form of an image, and the display module according to the exemplary embodiment of the present invention may correspond to a liquid crystal display (LCD), a plasma display panel (PDP), an organic light emitting diode (OLED), and may be manufactured by the display module manufacturing apparatus 10 according to the exemplary embodiment of the present invention.

In the meantime, a display device according to an exemplary embodiment of the present invention may include a display module, such as a TV and a computer monitor, manufactured by the display module manufacturing apparatus 10 according to the exemplary embodiment of the present invention.

In the above, although the present invention is described based on the limited exemplary embodiment and drawings, the present invention is not limited thereto, and but various changes and modifications may be made within the spirit of the present invention and the equivalent scope of the claims by those skilled in the art.

The invention claimed is:

1. An apparatus for manufacturing a display module, which attaches a polarizing plate, from which a release film is peeled, onto a display panel, the apparatus comprising:
   a separator configured to peel a release film from a polarizing plate; and
   a suction unit coupled to the separator to suck the foreign substances,
   wherein the separator includes:
   a main body;
   a peeling part extending in a longitudinal direction from one end of the main body, wherein the peeling part is in contact with the release film to peel the release film from the polarizing plate;
   a scattering preventing part to prevent foreign substances dropped from the release film when the release film is peeled from being scattered to the outside, wherein the scattering preventing part is spaced apart from the peeling part on a same surface of the main body, and wherein the scattering preventing part extends from the main body in a same direction as the peeling part;
   a first flow path, which is a partially enclosed space formed by the peeling part, the scattering preventing part and the main body, wherein the foreign substances removed from the release film are discharged into the first flow path;
   a second flow path passing through at least a part of an internal side of the main body; and
   a through-hole connecting the first flow path to the second flow path so that the foreign substances discharged into the first flow path are movable to the second flow path.

2. The apparatus of claim 1, wherein the second flow path is provided in a pair, and the pair of second flow paths is separated from each other based on a center portion of the main body and is positioned so as to face each other.

3. The apparatus of 4 claim 1, wherein the suction unit is coupled to the second flow path.

4. The apparatus of claim 1, wherein the suction unit includes a vacuum ejector or a vacuum pump.

* * * * *